United States Patent
De La Mettrie et al.

(10) Patent No.: US 6,342,078 B1
(45) Date of Patent: *Jan. 29, 2002

(54) OXIDATION DYEING COMPOSITION FOR KERATIN FIBRES AND DYEING METHOD USING SAID COMPOSITION

(75) Inventors: Roland De La Mettrie, Le Vesinet; Jean Cotteret, Verneuil-sur-Seine; Arnaud De Labbey, Aulnay Sous Bois; Mireille Maubru, Chatou, all of (FR)

(73) Assignee: L'Oreal, S. A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,203

(22) PCT Filed: Sep. 28, 1998

(86) PCT No.: PCT/FR98/02078

§ 371 Date: Jun. 30, 1999

§ 102(e) Date: Jun. 30, 1999

(87) PCT Pub. No.: WO99/17733

PCT Pub. Date: Apr. 15, 1999

(30) Foreign Application Priority Data

Oct. 3, 1997 (FR) .............................. 97/12350

(51) Int. Cl.$^7$ .............................. C09B 67/00
(52) U.S. Cl. .................. 8/401; 8/408; 8/409; 8/410; 8/411; 8/412; 8/416; 8/421; 8/424
(58) Field of Search .................. 8/401, 408, 409, 8/410, 411, 412, 416, 421, 424

(56) References Cited

U.S. PATENT DOCUMENTS

| | | | |
|---|---|---|---|
| 3,907,799 A | | 9/1975 | O'Brien et al. .............. 544/281 |
| 4,092,102 A | * | 5/1978 | Halasz et al. .................. 8/411 |
| 4,323,360 A | * | 4/1982 | Bugaut et al. .................. 8/412 |
| 4,324,553 A | * | 4/1982 | Bugaut et al. .................. 8/411 |
| 4,452,603 A | * | 6/1984 | Konrad et al. .................. 8/411 |
| 4,566,876 A | * | 1/1986 | Brown et al. .................. 8/411 |
| 4,854,935 A | * | 8/1989 | Clausen et al. ................. 8/411 |
| 4,961,925 A | | 10/1990 | Tsujino et al. .................. 8/401 |
| 5,224,965 A | * | 7/1993 | Clausen et al. ................. 8/411 |
| 5,690,696 A | * | 11/1997 | Bone et al. ..................... 8/411 |
| 5,833,969 A | * | 11/1998 | Tsujino et al. ........... 424/70.122 |
| 5,849,041 A | * | 12/1998 | Kunz et al. ..................... 8/408 |
| 5,863,300 A | * | 1/1999 | Audousset et al. ............. 8/411 |
| 6,027,719 A | * | 2/2000 | Tomura et al. .......... 424/78.02 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 195 47 991 | 6/1997 |
| EP | 0 310 675 | 4/1989 |
| EP | 0 628 559 | 12/1994 |
| EP | 0 716 846 | 6/1996 |
| EP | 0 766 958 | 4/1997 |
| EP | 0 795 313 | 9/1997 |
| FR | 2 586 913 | 3/1987 |
| FR | 2 733 749 | 11/1996 |
| GB | 1 026 978 | 4/1966 |
| GB | 1 153 196 | 5/1969 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 97/24105 | 7/1997 |
| WO | 98/22078 | * 5/1998 |

OTHER PUBLICATIONS

Vishnu J. Ram et al., "Synthesis of bioisosteric pyrazolo[1, 5–a]pyrimidines as leishmanicides", Indian Journal of Chemistry, vol. 34B, Jun. 1995, pp. 514–520.

Nadia S. Ibraham et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Robert H. Springer et al., "Synthesis and Enzymic Activity of 6–Carbethoxy–and 6–Ethoxy–3,7–disubstituted–pyrazolo[1,5–α]pyrimidines and Related Derivatives as Adenosine Cyclic 3',5'–Phosphate Phosphodiesterase Inhibitors", Journal of Medicinal Chemistry, vol. 25, No. 3, 1982, pp. 235–242.

Thomas Novinson et al., "Synthesis and Antifungal Properties of Certain 7–Alkylaminopyrazolo[1,5–a]pyrimidines", Journal of Medicinal Chemistry, vol. 20, No. 2, 1977, pp. 296–299.

Alexander McKillop et al., "Reaction of Hydrazine with β–Aminocrotononitrile: Synthesis of 2,7–dimethyl–5–aminopyrazolo[1,5–a]pyrimidine", Heterocycles, vol. 6, Nos. 9, 10, 1977, pp. 1355–1360.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

(List continued on next page.)

*Primary Examiner*—Yogendra N. Gupta
*Assistant Examiner*—D Hamlin
(74) *Attorney, Agent, or Firm*—Finnegan, Henderson, Farabow, Garrett & Dunner, L.L.P.

(57) ABSTRACT

The invention relates to a ready-to-use composition for the oxidation dyeing of keratin fibers, and in particular human keratin fibers such as the hair, comprising, in a medium which is suitable for dyeing, at least one oxidation base, at least one substituted meta-phenylenediamine as first coupler, at least one second coupler chosen from meta-aminophenols and meta-diphenols and at least one enzyme of 2-electron oxidoreductase type in the presence of at least one donor for the said enzyme, and to the dyeing process using this composition.

50 Claims, No Drawings

OTHER PUBLICATIONS

Ermitas Alcade et al., "Etude de la réaction du β–aminocrotonitrile et du α–formyl phénylacétonitile avec l'hydrazine: synthèse d'amino–7 pyrazolo[1,5–a]pyrimidines", Journal of Heterocyclic Chemistry, vol. 11, No. 3, Jun. 1974, pp. 423–429.
English language Derwent Abstract of DE 23 59 399, 6/75.
English language Derwent Abstract of DE 38 43 892, 6/90.
English language Derwent Abstract of DE 41 33 957, 4/93.
English language Derwent Abstract of DE 195 43 988, 5/97.
English language Derwent Abstract of DE 195 47 991, 6/97.
English language Derwent Abstract of EP 0 766 958, 4/97.
English language Derwent Abstract of EP 0 795 313, 9/97.
English language Derwent Abstract of FR 2 586 913, 3/87.
English language Derwent Abstract of FR 2 733 749, 11/96.
English language Derwent Abstract of JP 2019576, 1/90.
English language Derwent Abstract of JP 9–110659, 4/97.

* cited by examiner

OXIDATION DYEING COMPOSITION FOR KERATIN FIBRES AND DYEING METHOD USING SAID COMPOSITION

The invention relates to a composition for the oxidation dyeing of keratin fibres, and in particular human keratin fibres such as the hair, comprising, in a medium which is suitable for dyeing, at least one oxidation base, at least one substituted meta-phenylenediamine as first coupler, at least one second coupler chosen from meta-aminophenols and meta-diphenols and at least one enzyme of 2-electron oxidoreductase type in the presence of at least one donor for the said enzyme, and to the dyeing process using this composition.

It is known to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide have the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation base and optionally a coupler, in combination with enzymes such as pyranose oxidase, glucose oxidase or uricase, in the presence of a donor for the said enzymes. Although being used under conditions which do not result in a degradation of the keratin fibres which is comparable to that caused by the dyes used in the presence of hydrogen peroxide, these dyeing processes nevertheless lead to colorations which are not entirely satisfactory, in particular as regards their intensity and resistance to the various attacking factors to which the hair may be subjected.

The Applicant has now discovered that it is possible to obtain new dyes, which are capable of leading to intense colorations, without giving rise to any significant degradation of the keratin fibres, and which are relatively unselective and show good resistance to the various attacking factors to which the hair may be subjected, by combining at least one oxidation base, at least one substituted meta-phenylenediamine as first coupler, at least one second coupler chosen from meta-aminophenols and meta-diphenols and at least one enzyme of 2-electron oxidoreductase type in the presence of at least one donor for the said enzyme.

This discovery forms the basis of the present invention.

A first subject of the invention is thus a ready-to-use composition for the oxidation dyeing of keratin fibres, and in particular human keratin fibres such as the hair, characterized in that it comprises, in a medium which is suitable for dyeing:
  at least one oxidation base,
  at least one first coupler chosen from the meta-phenylenediamines of formula (I) below, and the addition salts thereof with an acid:

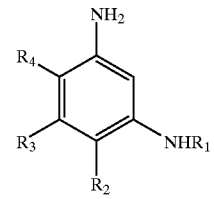

(I)

in which:
  $R_1$ represents a hydrogen atom or a $C_1$–$C_4$ alkyl, $C_1$–$C_4$ monohydroxyalkyl or $C_2$–$C_4$ polyhydroxyalkyl radical;
  $R_2$ and $R_3$, which may be identical or different, represent a hydrogen atom or a $C_1$–$C_4$ alkyl, $C_1$–$C_4$ monohydroxyalkoxy or $C_2$–$C_4$ polyhydroxyalkoxy radical;
  $R_4$ represents a hydrogen atom, a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxyalkoxy radical; it being understood that at least one of the radicals $R_1$ to $R_4$ is other than a hydrogen atom,
  at least one second coupler chosen from meta-aminophenols and meta-diphenols,
  at least one enzyme of 2-electron oxidoreductase type, and
  at least one donor for the said enzyme;
it not being possible for the said composition simultaneously to contain the combination of 2-amino-4-N-(β-hydroxyethyl)amino-1-methoxybenzene, 4-amino-3-methylphenol and 5-amino-2-methylphenol.

The ready-to-use dye composition in accordance with the invention leads to intense, relatively unselective colorations with excellent properties of resistance both to atmospheric agents such as light and bad weather and to perspiration and the various treatments to which the hair may be subjected (washing, permanent-waving).

A subject of the invention is also a process for the oxidation dyeing of keratin fibres using this ready-to-use dye composition.

Among the meta-phenylenediamines of formula (I) above, mention may be made more particularly of 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxy-propyloxy)benzene, 2,4-diamino-1-(β-hydroxyethyloxy)benzene and 2-amino-4-N-(β-hydroxyethyl)amino-1-methoxybenzene, and the addition salts thereof with an acid.

The 2-electron oxidoreductase(s) used in the ready-to-use dye composition in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made of uricase extracted from boar liver, uricase from *Arthrobacter globiformis,* as well as uricase from *Aspergillus flavus.*

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the ready-to-use dye composition, and even more preferably from 0.1 to 5i by weight approximately relative to this weight.

According to the invention, the term donor is understood to refer to the various substrates involved in the functioning of the said 2-electron oxidoreductase(s).

The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% by weight approximately relative to this weight.

The nature of the oxidation base(s) used in the ready-to-use dye composition is not a critical factor. They can be chosen, in particular, from para-phenylenediamines, double bases, para-aminophenols, ortho-aminophenols and heterocyclic oxidation bases.

Among the para-phenylenediamines which can be used as oxidation bases in the dye compositions in accordance with the invention, mention may be made in particular of the compounds of formula (II) below, and the addition salts thereof with an acid:

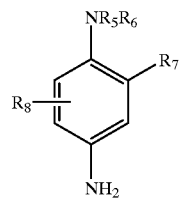

(II)

in which:
R$_5$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ alkyl radical substituted with a nitrogenous group, a phenyl radical or a 4'-aminophenyl radical;

R$_6$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous group;

R$_7$ represents a hydrogen atom, a halogen atom such as a chlorine, bromine, iodine or fluorine atom, a C$_1$–C$_4$ alkyl radical, a C$_1$–C$_4$ monohydroxyalkyl radical, a C$_1$–C$_4$ hydroxyalkoxy radical, an acetylamino(C$_1$–C$_4$)-alkoxy radical, a C$_1$–C$_4$ mesylaminoalkoxy radical or a carbamoylamino(C$_1$–C$_4$)alkoxy radical, R$_8$ represents a hydrogen or halogen atom or a C$_1$–C$_4$ alkyl radical.

Among the nitrogenous groups of formula (II) above, mention may be made in particular of amino, mono(C$_1$–C$_4$)alkylamino, di(C$_1$–C$_4$)alkylamino, tri(C$_1$–C$_4$)-alkylamino, monohydroxy(C$_1$–C$_4$)alkylamino, imidazolinium and ammonium radicals.

Among the para-phenylenediamines of formula (II) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl) aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxy-methyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylamino-ethyloxy-para-phenylenediamine and N-(β-methoxyethyl)-para-phenylenediamine, and the addition salts thereof with an acid.

Among the para-phenylenediamines of formula (II) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-paraphenylenediamine, 2-chloro-para-phenylenediamine and 2-β-acetylaminoethyloxy-para-phenylenediamine and the addition salts thereof with an acid are most particularly preferred.

According to the invention, the term double bases is understood to refer to the compounds containing at least two aromatic rings bearing amino and/or hydroxyl groups.

Among the double bases which can be used as oxidation bases in the dye compositions in accordance with the invention, mention may be made in particular of the compounds corresponding to formula (III) below, and the addition salts thereof with an acid:

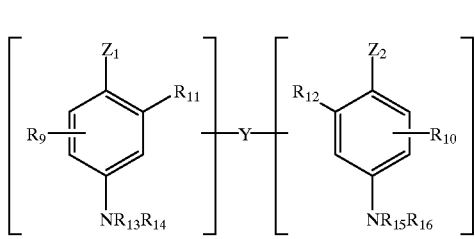

(III)

in which:
Z$_1$ and Z$_2$, which may be identical or different, represent a hydroxyl or —NH$_2$ radical which may be substituted with a C$_1$–C$_4$ alkyl radical or with a linker arm Y;
the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or C$_1$–C$_6$ alkoxy radicals;
R$_9$ and R$_{10}$ represent a hydrogen or halogen atom, a C$_1$–C$_4$ alkyl radical, a C$_1$–C$_4$ monohydroxyalkyl radical, a C$_2$–C$_4$ polyhydroxyalkyl radical, a C$_1$–C$_4$ aminoalkyl radical or a linker arm Y;
R$_{11}$, R$_{12}$, R$_{13}$, R$_{14}$, R$_{15}$ and R$_{16}$, which may be identical or different, represent a hydrogen atom, a linker arm Y or a C$_1$–C$_4$ alkyl radical;
it being understood that the compounds of formula (III) contain only one linker arm Y per molecule.

Among the nitrogenous groups of formula (III) above, mention may be made in particular of amino, mono(C$_1$–C$_4$)alkylamino, di(C$_1$–C$_4$)alkylamino, tri(C$_1$–C$_4$)-alkylamino, monohydroxy(C$_1$–C$_4$)alkylamino, imidazolinium and ammonium radicals.

Among the double bases of formula (III) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (III), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds corresponding to formula (IV) below, and the addition salts thereof with an acid:

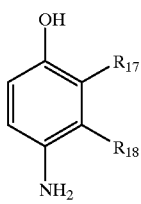

(IV)

in which:
R$_{17}$ represents a hydrogen or halogen atom or a C$_1$–C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy(C$_1$–C$_4$) alkylamino(C$_1$–C$_4$)alkyl radical,
R$_{18}$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy-(C$_1$–C$_4$)alkyl radical,
it being understood that at least one of the radicals R$_{17}$ or R$_{18}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-10659 or patent applications WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4- diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo [1,5-a] pyrimidines of formula (V) below, and the addition salts thereof with an acid or with a base and the tautomeric forms thereof, when a tautomeric equilibrium exists:

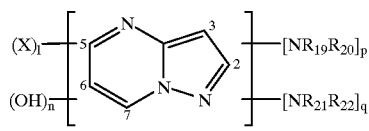

(V)

in which:

R$_{19}$, R$_{20}$, R$_{21}$ and R$_{22}$, which may be identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ aminoalkyl radical (it being possible for the amine to be protected with an acetyl, ureido or sulphonyl radical), a (C$_1$–C$_4$)alkylamino(C$_1$–C$_4$)alkyl radical, a di [(C$_1$–C$_4$)alkyl]amino(C$_1$–C$_4$)alkyl radical (it being possible for the dialkyl radicals to form a 5- or 6-membered carbon-based ring or a heterocycle), a hydroxy(C$_1$–C$_4$)alkyl- or di[hydroxy-(C$_1$–C$_4$)alkyl]amino(C$_1$–C$_4$)alkyl radical;

the radicals X, which may be identical or different, denote a hydrogen atom, a C$_1$14 C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$)alkylamino(C$_1$–C$_4$)alkyl radical, a di[(C$_1$–C$_4$)-alkyl]amino(C$_1$–C$_4$)alkyl radical (it being possible for the dialkyls to form a 5- or 6-membered carbon-based ring or a heterocycle), a hydroxy(C$_1$–C$_4$)alkyl- or di-[hydroxy(C$_1$–C$_4$)alkyl]amino(C$_1$–C$_4$)alkyl radical, an amino radical, a (C$_1$–C$_4$)alkyl- or di[(C$_1$–C$_4$)alkyl] amino radical; a halogen atom, a carboxylic acid group, a sulphonic acid group;

i is equal to 0, 1, 2 or 3;
p is equal to 0 or 1;
q is equal to 0 or 1;
n is equal to 0 or 1;

with the proviso that:
the sum p+q is other than 0;
when p+q is equal to 2, then n is equal to 0 and the groups NR$_{19}$R$_{20}$ and NR$_{21}$R$_{22}$ occupy the (2,3); (5,6); (6,7); (3,5) or (3,7) positions;

when p+q is equal to 1, then n is equal to 1 and the group NR$_{19}$R$_{20}$ (or NR$_{21}$R$_{22}$) and the OH group occupy the (2,3); (5,6); (6,7); (3,5) or (3,7) positions.

When the pyrazolo[1,5-a]pyrimidines of formula (V) above are such that they contain a hydroxyl group on one of the positions 2, 5 or 7 α to a nitrogen atom, a tautomeric equilibrium exists represented, for example, by the following scheme:

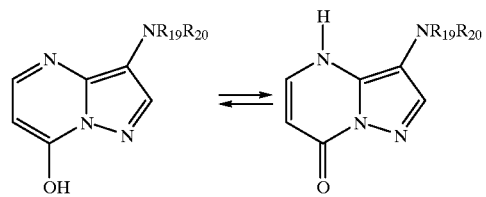

Among the pyrazolo[1,5-a]pyrimidines of formula (V) above, mention may be made in particular of:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and the addition salts thereof and the tautomeric forms thereof, when a tautomeric equilibrium exists.

The pyrazolo[1,5-a]pyrimidines of formula (V) above can be prepared by cyclization starting with an aminopyrazole, according to the syntheses described in the following references:

EP 628559 Beiersdorf-Lilly.
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN Pharmaceuticals.

The pyrazolo[1,5-a]pyrimidines of formula (V) above can also be prepared by cyclization starting from hydrazine, according to the syntheses described in the following references:

A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) preferably represent(s) from 0.0005 to 12% by weight approximately relative to the total weight of the dye composition in accordance with the invention, and even more preferably from 0.005 to 8% by weight approximately relative to this weight.

The meta-aminophenol(s) which can be used as second coupler in the ready-to-use dye composition in accordance with the invention is (are) preferably chosen from the compounds of formula (VI) below, and the addition salts thereof with an acid:

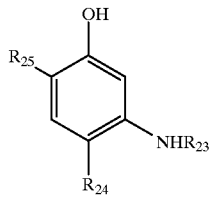

(VI)

in which:
R$_{23}$ represents a hydrogen atom or a C$_1$–C$_4$ alkyl, C$_1$–C$_4$ monohydroxyalkyl or C$_2$–C$_4$ polyhydroxyalkyl radical,
R$_{24}$ represents a hydrogen atom, a C$_1$–C$_4$ alkyl or C$_1$–C$_4$ alkoxy radical or a halogen atom chosen from chlorine, bromine and fluorine,
R$_{25}$ represents a hydrogen atom or a C$_1$–C$_4$ alkyl, C$_1$–C$_4$ alkoxy, C$_1$–C$_4$ monohydroxyalkyl, C$_2$–C$_4$ polyhydroxyalkyl, C$_1$–C$_4$ monohydroxyalkoxy or C$_2$–C$_4$ polyhydroxyalkoxy radical.

Among the meta-aminophenols of formula (VI) above, mention may be made more particularly of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxypropylamino)-2-methylphenol, and the addition salts thereof with an acid.

The meta-diphenol(s) which can be used as second coupler in the ready-to-use dye composition in accordance with the invention is (are) preferably chosen from the compounds of formula (VII) below, and the addition salts thereof with an acid:

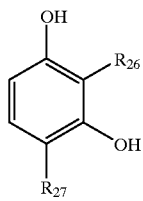

(VII)

in which
R$_{26}$ and R$_{27}$, which may be identical or different, represents a hydrogen atom, a C$_1$–C$_4$ alkyl radical or a halogen atom chosen from chlorine, bromine and fluorine.

Among the meta-diphenols of formula (VII) above, mention may be made more particularly of 1,3-dihydroxybenzene, 2-methyl-1,3-dihydroxybenzene, 4-chloro-1,3-dihydroxybenzene and 2-chloro-1,3-dihydroxybenzene, and the addition salts thereof with an acid.

The meta-phenylenediamine(s) of formula (I) above and/or the addition salt(s) thereof with an acid preferably represent(s) from 0.0001 to 56% by weight approximately relative to the total weight of the dye composition, and even more preferably from 0.005 to 3% by weight approximately relative to this weight.

The meta-aminophenol(s) and/or the meta-diphenol(s) which can be used as second coupler preferably represent(s) from 0.0001 to 8% by weight approximately relative to the total weight of the dye composition, and even more preferably from 0.005 to 5% by weight approximately relative to this weight.

The dye composition in accordance with the invention can also contain one or more direct dyes, in particular in order to modify the shades or to enrich them with glints.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the ready-to-use dye composition in accordance with the invention generally consists of water or a mixture of water and at least one organic solvent to dissolve the compounds which would not be sufficiently soluble in water. By way of organic solvents, mention may be made, for example, of C$_1$–C$_4$ alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the ready-to-use composition in accordance with the invention is chosen such that the enzymatic activity of the 2-electron oxidoreductase is sufficient. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (VIII) below:

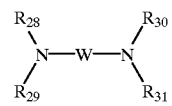

(VIII)

in which W is a propylene residue optionally substituted with a hydroxyl group or a C$_1$–C$_4$ alkyl radical; R$_{28}$, R$_{29}$, R$_{30}$ and R$_{31}$, which may be identical or different, represent a hydrogen atom or a C$_1$–C$_4$ alkyl or C$_1$–C$_4$ hydroxyalkyl radical.

The ready-to-use dye composition in accordance with the invention can also contain various adjuvants used conventionally in compositions for the dyeing of the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners such as, for example, silicones which may or may not be volatile or modified, film-forming agents, ceramides, preserving agents and opacifiers.

Needless to say, a person skilled in the art will take care to select this or these optional complementary compound(s) such that the advantageous properties intrinsically associated with the ready-to-use dye composition in accordance with the invention are not, or are not substantially, adversely affected by the addition or additions envisaged.

The ready-to-use dye composition in accordance with the invention can be in various forms, such as in the form of liquids, creams or gels, which may be pressurized, or in any other form which is suitable for dyeing keratin fibres, and in particular human hair. In this case the oxidation dyes and the 2-electron oxidoreductase(s) are present in the same ready-to-use composition, and consequently the said composition must be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is usually between 3 and 60 minutes and even more precisely between 5 and 40 minutes.

According to one specific embodiment of the invention, the process includes a preliminary step which consists in separately storing, on the one hand, a composition (A) comprising, in a medium which is suitable for dyeing, at least one oxidation base and at least one meta-phenylenediamine of formula (I) as defined above as first coupler, at least one second coupler chosen from meta-aminophenols and meta-diphenols, and, on the other hand, a composition (B) comprising, in a medium which is suitable for dyeing, at least one enzyme of 2-electron oxidoreductase type in the presence of at least one donor for the said enzyme, and then in mixing them together at the time of use, after which this mixture is applied to the keratin fibres.

Another subject of the invention is a multi-compartment dyeing device or "kit" or any other multi-compartment packaging system, a first compartment of which comprises composition (A) as defined above and a second compartment of which comprises composition (B) as defined above. These devices can be equipped with means for delivering the desired mixture onto the hair, such as the devices described in patent FR-2,586,913 in the name of the Applicant.

The examples which follow are intended to illustrate the invention without, however, limiting its scope.

EXAMPLES

Dyeing Examples 1 to 5

The ready-to-use dye compositions below were prepared (contents in grams):

| COMPOSITION | 1 | 2 | 3 | 4 | 5 |
|---|---|---|---|---|---|
| para-Phenylenediamine (oxidation base) | 0.216 | 0.108 | 0.108 | 0.216 | 0.216 |
| 2,4-Diamino-1-(β-hydroxyethyloxy)benzene dihydrochloride (coupler) | 0.048 | — | — | 0.048 | — |
| 2-Amino-4-N-(β-hydroxyethyl)amino-methoxybenzene dihydrochloride (coupler) | — | 0.028 | 0.028 | — | 0.056 |
| 1,3-Dihydroxybenzene (coupler) | 0.198 | 0.100 | — | — | — |
| meta-Aminophenol (coupler) | — | — | 0.100 | — | — |
| 5-Amino-2-methylphenol | — | — | — | 0.22 | 0.05 |
| para-Aminophenol (oxidation base) | — | — | — | — | 0.1 |
| Uricase from Arthrobacter globiformis, at 20 International Units (I.U.)/mg, sold by the company Sigma | 1.5 | 1.5 | 1.5 | 1.5 | 1.5 |
| Uric acid | 1.5 | 1.5 | 1.5 | 1.5 | 1.5 |
| Common dye support (*) | (*) | (*) | (*) | (*) | (*) |
| Demineralized water qs | 100 g | 100 g | 100 g | 100 g | 100 g |

(*): Common dye support

Ethanol 20.0 g

Hydroxyethylcellulose sold under the name Natrosol 250 HR® by the company Aqualon 1.0 g Poly($C_8$–$C_{10}$)alkylglucoside as an aqueous solution containing 60% active material (A.M.) buffered with ammonium citrate (0.5%), sold under the name Oramix CG110® by the company SEPPIC 8.0 g Monoethanolamine qs pH=9.5

Each of the ready-to-use dye compositions described above was applied to locks of natural grey hair containing 90% white hairs, for 30 minutes. The hair was then rinsed, washed with a standard shampoo and then dried.

The hair was dyed in the shades given in the table below:

| EXAMPLE | Shade obtained |
|---|---|
| 1 | Dark blonde |
| 2 | Light blonde |
| 3 | Pearlescent blonde |
| 4 | Dark mahogany blonde |
| 5 | Pearlescent blonde |

What is claimed is:

1. A ready-to-use composition for the oxidation dyeing of keratin fibers comprising:

at least one solvent chosen from water and organic solvents, at least one oxidation base, at least one first coupler chosen from the meta-phenylenediamines of formula (I) below, and acid-addition salts thereof:

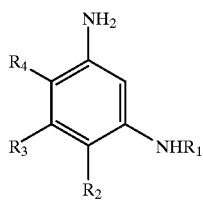

in which:
- $R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals;
- $R_2$ and $R_3$, which may be identical or different, are chosen from a hydrogen atom, $C_1$–$C_4$ alkyl radicals, $C_1$–$C_4$ monohydroxyalkoxy radicals and $C_2$–$C_4$ polyhydroxyalkoxy radicals;
- $R_4$ is chosen from a hydrogen atom, $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and 2,4-diaminophenoxyalkoxy radicals; and wherein at least one of said radicals $R_1$ to $R_4$ is a radical other than a hydrogen atom, at least one second coupler chosen from meta-aminophenols, meta-diphenols and acid-addition salts thereof, at least one enzyme chosen from 2-electron oxidoreductases, at least one donor for said enzyme; and
wherein said composition does not contain the combination of 2-amino-4-N-(β-hydroxyethyl)amino-1-methoxybenzene, 4-amino-3-methylphenol and 5-amino-2-methylphenol.

2. The composition according to claim 1, wherein said keratin fibers are human keratin fibers.

3. The composition according to claim 2, wherein said human keratin fibers are human hair.

4. The composition according to claim 1, wherein said at least one first coupler is chosen from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1 -ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino-4-N-(β-hydroxyethyl)amino-1-methoxybenzene, and acid-addition salts thereof.

5. The composition according to claim 1, wherein said at least one first coupler is present in an amount ranging from 0.0001 to 5% by weight relative to the total weight of the composition.

6. The composition according to claim 5, wherein said at least one first coupler is present in an amount ranging from 0.005 to 3% by weight relative to the total weight of the composition.

7. The composition according to claim 1, wherein said at least one enzyme is chosen from pyranose oxidases, glucose oxidases, glycerol oxidases, lactate oxidases, pyruvate oxidases and uricases.

8. The composition according to claim 1, wherein said at least one enzyme is chosen from uricases of animal, microbiological and biotechnological origin.

9. The composition according to claim 1, wherein said at least one enzyme is present in an amount ranging from 0.01 to 20% by weight relative to the total weight of said composition.

10. The composition according to claim 9, wherein said at least one enzyme is present in an amount ranging from 0.1 to 5% by weight relative to the total weight of said composition.

11. The composition according to claim 1, wherein said at least one donor for said enzyme is chosen from D-glucose, L-sorbose, D-xylose, glycerol, dihydroxyacetone, lactic acid and salts thereof; pyruvic acid and salts thereof; and uric acid and salts thereof.

12. The composition according to claim 11, wherein said at least one donor for said enzyme is chosen from uric acid and its salts.

13. The composition according to claim 1, wherein said at least one donor for said enzyme is present in an amount ranging from 0.01 to 20% by weight relative to the total weight of said composition.

14. The composition according to claim 13, wherein said at least one donor for said enzyme is present in an amount ranging from 0.1 to 5% by weight relative to the total weight of said composition.

15. The composition according to claim 1, wherein said at least one oxidation base is chosen from para-phenylenediamines, double bases, para-aminophenols, ortho-aminophenols, heterocyclic bases and acid-addition salts thereof.

16. The composition according to claim 15, wherein said para-phenylenediamines are chosen from para-phenylenediamines of formula (II) below, and acid-addition salts thereof:

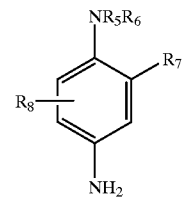

in which:
- $R_5$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals, $C_1$–$C_4$ alkyl radicals substituted with a nitrogenous group, a phenyl radical and a 4'-aminophenyl radical;
- $R_6$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals and $C_1$–$C_4$ alkyl radicals substituted with a nitrogenous group;
- $R_7$ is chosen from a hydrogen atom, halogen atoms, $C_1$–$C_4$ alkyl radicals, $C_1$–$C_4$ monohydroxyalkyl radicals, $C_1$–$C_4$ hydroxyalkoxy radicals, acetylamino $(C_1$–$C_4)$alkoxy radicals, $C_1$–$C_4$ mesylaminoalkoxy radicals and carbamoylamino$(C_1$–$C_4)$alkoxy radicals, and
- $R_8$ is chosen from a hydrogen, halogen atoms and $C_1$–$C_4$ alkyl radicals.

17. The composition of claim 16, wherein said halogen atoms are chosen from chlorine, bromine, iodine and fluorine atoms.

18. The composition according to claim 16, wherein said para-phenylenediamines of formula (II) are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof.

19. The composition according to claim 15, wherein said double bases are chosen from double bases of formula (III) below, and acid-addition salts thereof:

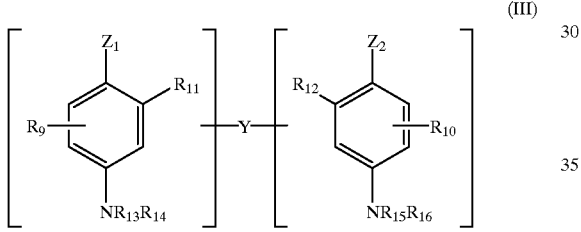

(III)

in which:
Z$_1$ and Z$_2$, which may be identical or different, are chosen from a hydroxyl radical, an —NH$_2$ radical optionally substituted with C$_1$–C$_4$ alkyl radicals or with a linker arm Y;

the linker arm Y is chosen from linear and branched alkylene chains containing from 1 to 14 carbon atoms, which may be interrupted by or terminated with at least one entity chosen from nitrogenous groups and hetero atoms, and optionally having at least one substituent chosen from hydroxyl and C$_1$–C$_6$ alkoxy radicals;

R$_9$ and R$_{10}$, which may be identical or different, are chosen from a hydrogen atom, halogen atoms, C$_1$–C$_4$ alkyl radicals, C$_1$–C$_4$ monohydroxyalkyl radicals, C$_2$–C$_4$ polyhydroxyalkyl radicals, C$_1$–C$_4$ aminoalkyl radicals and a linker arm Y;

R$_{11}$, R$_{12}$, R$_{13}$, R$_{14}$, R$_{15}$ and R$_{16}$, which may be identical or different, are chosen from a hydrogen atom, a linker arm Y and C$_1$–C$_4$ alkyl radicals; and wherein said compounds of formula (III) and salts thereof contain only one linker arm Y per molecule.

20. The composition according to claim 19, wherein hetero atoms are chosen from oxygen, sulphur and nitrogen atoms.

21. The composition according to claim 19, wherein said double bases of formula (III) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)-tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid-addition salts thereof.

22. The composition according to claim 15, wherein said para-aminophenols are chosen from para-aminophenols of formula (IV) below, and acid-addition salts thereof:

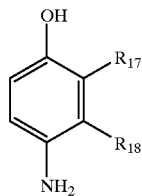

(IV)

in which:
R$_{17}$ is chosen from a hydrogen atom, halogen atoms, C$_1$–C$_4$ alkyl radicals, C$_1$–C$_4$ monohydroxyalkyl radicals, (C$_1$–C$_4$)alkoxy(C$_1$–C$_4$)alkyl radicals, C$_1$–C$_4$ aminoalkyl radicals and hydroxy(C$_1$–C$_4$)alkylamino (C$_1$–C$_4$)alkyl radicals, R$_{18}$ is chosen from a hydrogen atom, halogen atoms, C$_1$–C$_4$ alkyl radicals, C$_1$–C$_4$ monohydroxyalkyl radicals, C$_2$–C$_4$ polyhydroxyalkyl radicals, C$_1$–C$_4$ aminoalkyl radicals, C$_1$–C$_4$ cyanoalkyl radicals and (C$_1$–C$_4$)alkoxy-(C$_1$–C$_4$)alkyl radicals, wherein at least one of the radicals R$_{17}$ and R$_{18}$ is a hydrogen atom.

23. The composition according to claim 22, wherein said para-aminophenols of formula (IV) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof.

24. The composition according to claim 15, wherein said ortho-aminophenols are chosen from 2-aminophenol, 2-amino-5-methylphenol, 2-amino-6-methylphenol, 5-acetamido-2-aminophenol, and acid-addition salts thereof.

25. The composition according to claim 15, wherein said heterocyclic bases are chosen from pyridine compounds, pyrimidine compounds, pyrazole compounds, pyrazolopyrimidine compounds, and acid-addition salts thereof.

26. The composition according to claim 25, wherein said heterocyclic bases are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid-addition salts thereof, 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and acid-addition salts thereof, 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1- methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid-addition salts thereof, pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and addition salts thereof and tautomeric forms thereof, when a tautomeric equilibrium exists.

27. The composition according to claim 1, wherein said at least one oxidation base is present in an amount ranging from 0.0005 to 12% by weight relative to the total weight of the composition.

28. The composition according to claim 27, wherein said at least one oxidation base is present in an amount ranging from 0.005 to 8% by weight relative to the total weight of the composition.

29. The composition according to claim 1, wherein said at least one second coupler is chosen from meta-aminophenols of formula (VI) below, and acid-addition salts thereof:

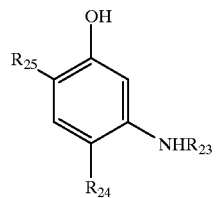

(VI)

in which:
R$_{23}$ is chosen from a hydrogen atom, C$_1$–C$_4$ alkyl radicals, C$_1$–C$_4$ monohydroxyalkyl radicals and C$_2$–C$_4$ polyhydroxyalkyl radicals,
R$_{24}$ is chosen from a hydrogen atom, C$_1$–C$_4$ alkyl radicals, C$_1$–C$_4$ alkoxy radicals, and halogen atoms, and
R$_{25}$ is chosen from a hydrogen atom, C$_1$–C$_4$ alkyl radicals, C$_1$–C$_4$ alkoxy radicals, C$_1$–C$_4$ monohydroxyalkyl radicals, C$_2$–C$_4$ polyhydroxyalkyl radicals, C$_1$–C$_4$ monohydroxyalkoxy radicals and C$_2$–C$_4$ polyhydroxyalkoxy radicals.

30. The composition according to claim 29, wherein said halogen atoms are chosen from chlorine, bromine and fluorine atoms.

31. The composition according to claim 29, wherein said at least one second coupler is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid-addition salts thereof.

32. The composition according to claim 1, wherein said at least one second coupler is chosen from meta-diphenols of formula (VII) below, and acid-addition salts thereof:

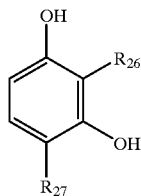

(VII)

in which:
R$_{26}$ and R$_{27}$, which may be identical or different, are chosen from a hydrogen atom, halogenatons, and C$_1$–C$_4$ alkyl radicals.

33. The composition according to claim 32, wherein said halogen atoms are chosen from chlorine, bromine, and fluorine atoms.

34. The composition according to claim 32, wherein said at least one second coupler is chosen from 1,3-dihydroxybenzene, 2-methyl-1,3-dihydroxybenzene, 4-chloro-1,3-dihydroxybenzene, 2-chloro-1,3-dihydroxybenzene, and acid-addition salts thereof.

35. The composition according to claim 1, wherein said at least one second coupler is present in an amount ranging from 0.0001 to 8% by weight relative to the total weight of the composition.

36. The composition according to claim 35, wherein said at least one second coupler is present in an amount ranging from 0.005 to 5% by weight relative to the total weight of the composition.

37. The composition according to claim 1, wherein said acid-addition salts are chosen from hydrochlorides, hydrobromides, sulphates, tartrates, lactates and acetates.

38. The composition according to claim 1, wherein said composition has a pH ranging from 5 to 11.

39. The composition according to claim 1, further comprising at least one peroxidase.

40. A ready-to-use composition for the oxidation dyeing of keratin fibers comprising:
an oxidation base chosen from para-phenylenediamine, para-aminophenol and acid-addition salts thereof;
a first coupler chosen from 2,4-diamino-1-(β-hydroxyethyloxy)benzene, 2-amino-4-N-(β-hydroxyethyl)amino-1-methoxybenzene, and acid-addition salts thereof;
a second coupler chosen from 1,3-dihydroxybenzene, meta-aminophenol, 5-amino-2-methylphenol, and acid-addition salts thereof;

an enzyme chosen from uricases; and
a donor chosen from uric acid and salts thereof.

41. A process for dyeing keratin fibers, comprising applying a ready-to-use composition for the oxidation dyeing of keratin fibers to said fibers and developing for a period sufficient to achieve the desired coloration, wherein said composition comprises:
- at least one solvent chosen from water and organic solvents,
- at least one oxidation base,
- at least one first coupler chosen from the meta-phenylenediamines of formula (I) below, and acid-addition salts thereof:

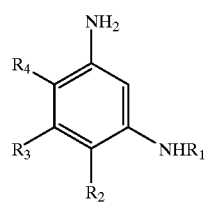

(I)

in which:
- $R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals;
- $R_2$ and $R_3$, which may be identical or different, are chosen from a hydrogen atom, $C_1$–$C_4$ alkyl radicals, $C_1$–$C_4$ monohydroxyalkoxy radicals and $C_2$–$C_4$ polyhydroxyalkoxy radicals;
- $R_4$ is chosen from a hydrogen atom, $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and a 2,4diaminophenoxyalkoxy radical; and
- wherein at least one of said radicals $R_1$ to $R_4$ is a radical other than a hydrogen atom,
- at least one second coupler chosen from meta-aminophenols, meta-diphenols and acid-addition salts thereof,
- at least one enzyme chosen from 2-electron oxidoreductases;
- at least one donor for said enzyme; and wherein said composition does not contain the combination of 2-amino-4-N-(β-hydroxyethyl)amino-1-methoxybenzene, 4-amino-3-methylphenol and 5-amino-2-methylphenol.

42. A process for dyeing keratin fibers, comprising applying a composition for the oxidation dyeing of keratin fibers to said fibers and developing for a period sufficient to achieve a desired coloration, wherein said composition comprises:
- an oxidation base chosen from para-phenylenediamine para-aminophenol and acid-addition salts thereof;
- a first coupler chosen from 2,4-diamino-1-(β-hydroxyethyloxy)benzene, 2-amino-4-N-(β-hydroxyethyl)amino-1-methoxybenzene para-aminophenol, and acid-addition salts thereof;
- a second coupler chosen from 1,3-dihydroxybenzene, meta-aminophenol, 5-amino-2methylphenol, and acid-addition salts thereof;
- an enzyme chosen from uricases; and
- a donor chosen from uric acid and salts thereof.

43. A process for dyeing keratin fibers, comprising:
separately storing a first composition,
separately storing a second composition,
thereafter mixing said first composition with said second composition,
applying said mixture to said keratin fibers, and
developing for a period of time sufficient to achieve a desired coloration,
wherein said first composition comprises:
- at least one oxidation base,
- at least one first coupler chosen from the meta-phenylenediamines of formula (I) below, and acid-addition salts thereof:

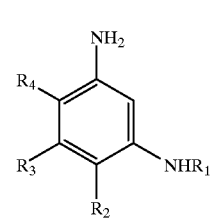

(I)

in which:
- $R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals;
- $R_2$ and $R_3$, which may be identical or different, are chosen from a hydrogen atom, $C_1$–$C_4$ alkyl radicals, $C_1$–$C_4$ monohydroxyalkoxy radicals and $C_2$–$C_4$ polyhydroxyalkoxy radicals;
- $R_4$ is chosen from a hydrogen atom, $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and a 2,4-diaminophenoxyalkoxy radical; and
- wherein at least one of said radicals $R_1$ to $R_4$ is a radical other than a hydrogen atom, and
- at least one second coupler chosen from meta-aminophenols, meta-diphenols, and acid-addition salts thereof, wherein said second composition comprises at least one enzyme chosen from 2-electron oxidoreductases and at least one donor for said enzyme; and wherein said first and second compositions do not contain the combination of 2-amino-4-N-(β-hydroxyethyl)amino-1-methoxybenzene, 4-amino-3-methylphenol and 5-amino-2-methylphenol.

44. A process for dyeing keratin fibers, comprising:
separately storing a first composition,
separately storing a second composition,
thereafter mixing said first composition with said second composition,
applying said mixture to said keratin fibers, and
developing for a period of time sufficient to achieve a desired coloration,
wherein said first composition comprises:
- at least one oxidation base chosen from:
  - para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-paraphenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof, double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N—bis(4'-amino-3'-methylphenyl)ethylenediamine, 1,8-bis(2,5-diaminophenoxy)-3,5-dioxaoctane, and acid-addition salts thereof, para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, ortho-aminophenols chosen from: 2-aminophenol, 2-amino-5-methyl phenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and acid-addition salts thereof, pyrazole compounds chosen from: 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol ;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and tautomeric forms thereof, when a tautomeric equilibrium exists;

at least one first coupler chosen from meta-phenylenediamines chosen from: 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene, and acid-addition salts thereof; and at least one second coupler chosen from:
meta-aminophenols chosen from: meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid-addition salts thereof, and meta-diphenols chosen from: 1,3-dihydroxybenzene, 2-methyl-1,3-dihydroxybenzene, 4-chloro-1,3-dihydroxybenzene, 2-chloro-1,3-dihydroxybenzene, and acid-addition salts thereof;

wherein said second composition comprises:
  at least one enzyme chosen from pyranose oxidases, glucose oxidases, glycerol oxidases, lactate oxidases, pyruvate oxidases and uricases; and
  a donor for said enzyme chosen from D-glucose, L-sorbose, D-xylose, glycerol, dihydroxyacetone, lactic acid and salts thereof; pyruvic acid and salts thereof; and uric acid and salts thereof;
wherein said first and second compositions do not contain the combination of 2-amino-4-N-(β-hydroxyethyl)amino-1-methoxybenzene, 4-amino-3-methylphenol and 5-amino-2-methylphenol.

45. A process for dyeing keratin fibers, comprising:
separately storing a first composition,
separately storing a second composition,
thereafter mixing said first composition with said second composition,
applying said mixture to said keratin fibers, and
developing for a period sufficient to achieve a desired coloration:
  wherein said first composition comprises:
    at least one solvent chosen from water and organic solvents;
    an oxidation base chosen from para-phenylenediamine, para-aminophenol, and acid-addition salts thereof,
    a first coupler chosen from 2,4-diamino-1-(β-hydroxyethyloxy)benzene, 2-amino-4-N-(β-hydroxyethyl)amino-1-methoxybenzene, and acid-addition salts thereof; and
    a second coupler chosen from 1,3-dihydroxybenzene, meta-aminophenol, 5-amino-2-methylphenol, and acid-addition salts thereof,
  wherein said first composition does not contain the combination of 2-amino-4-N-(β-hydroxyethyl)amino-1-methoxybenzene, 4-amino-3-methylphenol and 5-amino-2-methylphenol; and
  wherein said second composition comprises:
    an enzyme chosen from uricases; and
    a donor chosen from uric acid and salts thereof.

46. A multi-compartment dyeing kit, comprising a first compartment containing a first composition and second compartment containing a second composition,
  wherein said first composition comprises:
    at least one oxidation base,
    at least one first coupler chosen from the meta-phenylenediamines of formula (I) below, and acid-addition salts thereof:

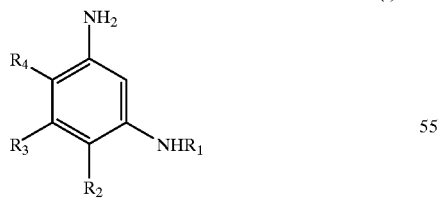

(I)

in which:
  $R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals;
  $R_2$ and $R_3$, which may be identical or different, are chosen from a hydrogen atom, $C_1$–$C_4$ alkyl radicals, $C_1$–$C_4$ monohydroxyalkoxy radicals and $C_2$–$C_4$ polyhydroxyalkoxy radicals;
  $R_4$ is chosen from a hydrogen atom, $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and a 2,4-diaminophenoxyalkoxy radical; and
  wherein at least one of said radicals $R_1$ to $R_4$ is a radical other than a hydrogen atom, and
  at least one second coupler chosen from meta-aminophenols, meta-diphenols and acid-addition salts thereof,
  wherein said second composition comprises at least one enzyme chosen from 2-electron oxidoreductases and at least one donor for said enzyme; and
  wherein said first and second compositions do not contain the combination of 2-amino-4-N-(β-hydroxyethyl)amino-1-methoxybenzene, 4-amino-3-methylphenol and 5-amino-2-methylphenol.

47. A multi-compartment dyeing kit, comprising a first compartment containing a first composition and second compartment containing a second composition,
  wherein said first composition comprises:
    at least one oxidation base chosen from:
      para-phenylenediamines chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof,
      double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid-addition salts thereof,
      para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β- hydroxyethylaminomethyl)phenol, 4-amino-2-fluorophenol, and acid-addition salts thereof, ortho-aminophenols chosen from: 2-aminophenol, 2-amino-5-methylphenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and acid-addition salts thereof, pyrazole compounds chosen from: 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and tautomeric forms thereof, when a tautomeric equilibrium exists;

at least one first coupler chosen from metaphenylenediamines chosen from: 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene, and acid-addition salts thereof; and at least one second coupler chosen from:
meta-aminophenols chosen from: meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid-addition salts thereof, and meta-diphenols chosen from: 1,3-dihydroxybenzene, 2-methyl-1,3-dihydroxybenzene, 4-chloro-1,3-dihydroxybenzene, 2-chloro-1,3-dihydroxybenzene, and acid-addition salts thereof;

wherein said second composition comprises:
at least one enzyme chosen from pyranose oxidases, glucose oxidases, glycerol oxidases, lactate oxidases, pyruvate oxidases and uricases; and
a donor for said enzyme chosen from D-glucose, L-sorbose, D-xylose, glycerol, dihydroxyacetone, lactic acid and salts thereof; pyruvic acid and salts thereof; and uric acid and salts thereof;

wherein said first and second compositions do not contain the combination of 2-amino-4-N-(β-hydroxyethyl)amino-1-methoxybenzene, 4-amino-3-methylphenol and 5-amino-2-methylphenol.

48. A multi-compartment dyeing kit, comprising a first compartment containing a first composition and second compartment containing a second composition, wherein said first composition comprises:
at least one solvent chosen from water and organic solvents;
an oxidation base chosen from para-phenylenediamine, para-aminophenol, and acid-addition salts thereof;
a first coupler chosen from 2,4-diamino-1-(β-hydroxyethyloxy)benzene, 2-amino-4-N-(β-hydroxyethyl)amino-1-methoxybenzene, and acid-addition salts thereof; and
a second coupler chosen from 1,3-dihydroxybenzene, meta-aminophenol, 5-amino-2-methylphenol, and acid-addition salts thereof;
wherein said first composition does not contain the combination of 2-amino-4-N-(β-hydroxyethyl)amino-1-methoxybenzene, 4-amino-3-methylphenol and 5-amino-2-methylphenol; and wherein said second composition comprises:
an enzyme chosen from uricases; and
a donor chosen from uric acid and salts thereof.

49. A ready-to-use composition for the oxidation dyeing of keratin fibers comprising:
at least one solvent chosen from water and organic solvents,
at least one oxidation base chosen from:

para-phenylenediamines chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, -(β-methoxyethyl)-para-phenylenediamine, and acid-addition salts thereof, double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)-tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid-addition salts thereof, para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, ortho-aminophenols chosen from: 2-aminophenol, 2-amino-5-methyl phenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid-addition salts thereof, pyrimidine compounds chosen from: 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and acid-addition salts thereof, pyrazole compounds chosen from: 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid-addition salts thereof, and pyrazolopyrimidine compounds chosen from:
pyrazolo[1,5-a]pyrimidine-3,7-diamine;
2,5-d imethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino) ethanol;
2-(7-aminopyrazolo[1,5-a]pyrimidin-3-ylamino) ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and addition salts thereof and the tautomeric forms thereof, when a tautomeric equilibrium exists;

at least one first coupler chosen from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene, and acid-addition salts thereof;

at least one second coupler chosen from:
meta-aminophenols chosen from: meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid-addition salts thereof, and meta-diphenols chosen from 1,3-dihydroxybenzene, 2-methyl-1,3-dihydroxybenzene, 4-chloro-1,3-dihydroxybenzene and 2-chloro-1,3-dihydroxybenzene, and acid-addition salts thereof;

at least one enzyme chosen from pyranose oxidases, glucose oxidases, glycerol oxidases, lactate oxidases, pyruvate oxidases and uricases;

at least one donor for said enzyme chosen from D-glucose, L-sorbose, D-xylose, glycerol, dihydroxyacetone, lactic acid and salts thereof; pyruvic acid and salts thereof; and uric acid and salts thereof; and wherein said composition does not contain the combination of 2-amino-4-N-(β-hydroxyethyl)amino-1-methoxybenzene, 4-amino-3-methylphenol and 5-amino-2-methylphenol.

50. A process for dyeing keratin fibers, comprising applying a ready-to-use composition for the oxidation dyeing of keratin fibers to said fibers and developing for a period sufficient to achieve the desired coloration, wherein said composition comprises:

at least one solvent chosen from water and organic solvents, at least one oxidation base chosen from:

para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and acid-addition salts thereof, double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis (2,5-diaminophenoxy)-3,5-dioxaoctane, and acid-addition salts thereof, para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and acid-addition salts thereof, ortho-aminophenols chosen from: 2-aminophenol, 2-amino-5-methylphenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and acid-addition salts thereof, pyrazole compounds chosen from: 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1, 5-a]pyrimidin-7-ol;
3-aminopyrazolo[1, 5-a]pyrimidin-5-ol;
2-(3-aminopyrazolo[1,5-a]pyrimidin-7-ylamino) ethanol;
2-(7-aminopyrazolo[1,5-a]pyrimidin-3-ylamino) ethanol;
2-[(3-aminopyrazolo[1,5-a]pyrimidin-7-yl)-(2-hydroxyethyl)amino]ethanol;
2-[(7-aminopyrazolo[1,5-a]pyrimidine-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5, N7, N7-tetramethylpyrazolo[1,5-a]pyrimidine-3,7-diamine;
and addition salts thereof and the tautomeric forms thereof, when a tautomeric equilibrium exists;

at least one first coupler chosen from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-

(β-hydroxyethyloxy)-1-methylbenzene, 2,4-diamino-1-(⊖,γ-dihydroxypropyloxy)benzene, 2,4-diamino-1-(β-hydroxyethyloxy)benzene, 2-amino-4-N-(β-hydroxyethyl)amino-1-methoxybenzene, and acid-addition salts thereof;

at least one second coupler chosen from:
meta-aminophenols chosen from: meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxypropylamino)-2-methylphenol, and acid-addition salts thereof, meta-diphenols chosen from: 1,3-dihydroxybenzene, 2-methyl-1,3-dihydroxybenzene, 4-chloro-1,3-dihydroxybenzene and 2-chloro-1,3-dihydroxybenzene, and acid-addition salts thereof, at least one enzyme chosen from pyranose oxidases, glucose oxidases, glycerol oxidases, lactate oxidases, pyruvate oxidases and uricases;

at least one donor for said enzyme chosen from D-glucose, L-sorbose, D-xylose, glycerol, dihydroxyacetone, lactic acid and salts thereof; pyruvic acid and salts thereof; and uric acid and salts thereof; and wherein said composition does not contain the combination of 2-amino-4-N-(β-hydroxyethyl)amino-1-methoxybenzene, 4-amino-3-methylphenol and 5-amino-2-methylphenol.

* * * * *

UNITED STATES PATENT AND TRADEMARK OFFICE
CERTIFICATE OF CORRECTION

PATENT NO. : 6,342,078 B1
DATED : January 29, 2002
INVENTOR(S) : Roland de la Mettrie et al.

It is certified that error appears in the above-identified patent and that said Letters Patent is hereby corrected as shown below:

Column 19,
Line 6, delete "the" and insert -- a -- therefor.

Column 21,
Line 67, replace ""butyl3" with -- butyl-3 --.

Column 28,
Line 18, delete the space after "2,5-d".

Column 31,
Line 2, replace "θ" with -- β --.

Signed and Sealed this

Sixth Day of August, 2002

Attest:

JAMES E. ROGAN
Attesting Officer     Director of the United States Patent and Trademark Office